United States Patent [19]

Eason

[11] Patent Number: 4,898,196
[45] Date of Patent: Feb. 6, 1990

[54] FLOSSING DEVICE

[76] Inventor: W. Jeter Eason, 150 Goodwyn, Memphis, Tenn. 38111

[21] Appl. No.: 348,964

[22] Filed: May 8, 1989

[51] Int. Cl.⁴ .............................................. A61C 15/00
[52] U.S. Cl. .................................... 132/327; 132/324; 132/326
[58] Field of Search ............... 132/323, 324, 325, 326, 132/327

[56] References Cited

U.S. PATENT DOCUMENTS

| | | | |
|---|---|---|---|
| 911,068 | 2/1909 | Perkins | 132/325 |
| 1,161,043 | 11/1915 | Gallas | 132/325 |
| 1,174,016 | 2/1916 | Kenyon | 132/325 |
| 1,465,669 | 8/1923 | Hochstadter | 132/324 |
| 1,733,631 | 10/1929 | Spiegel et al. | 132/324 |
| 1,966,463 | 7/1934 | Rose | 132/324 |
| 2,644,469 | 7/1953 | Cohen | 132/324 |
| 3,835,872 | 9/1974 | Daniel | 132/324 |
| 4,655,234 | 4/1987 | Bowden | 132/325 |
| 4,660,584 | 4/1987 | Wofford | 132/325 |

*Primary Examiner*—John J. Wilson
*Attorney, Agent, or Firm*—Walker & Mckenzie

[57] ABSTRACT

A flossing device including a handle, the handle having a forward end, having a hollow interior for holding dental floss and having an aperture extending from the hollow interior for allowing the distal end of the dental floss to extend outward from the hollow interior; a first arm member extending outward from the forward end of the handle, the first arm member having an outer end positioned a spaced distance from the forward end of the handle; a second arm member extending outward from the forward end of the handle, the second arm member having an outer end positioned a spaced distance from the forward end of the handle and from the outer end of the first arm member; and structure for positioning a portion of the distal end of the dental floss between the outer end of the first arm member and the outer end of the second arm member and for holding the portion of the distal end of the dental floss tight between the outer end of the first arm member and the outer end of the second arm member, the positioning structure including a first lock mechanism for locking the dental floss relative to the first arm member, and a second lock means for locking the dental floss relative to the scond arm member, one of the lock mechanisms being spring activated to automatically lock the dental floss relative to one of the arm members.

4 Claims, 1 Drawing Sheet

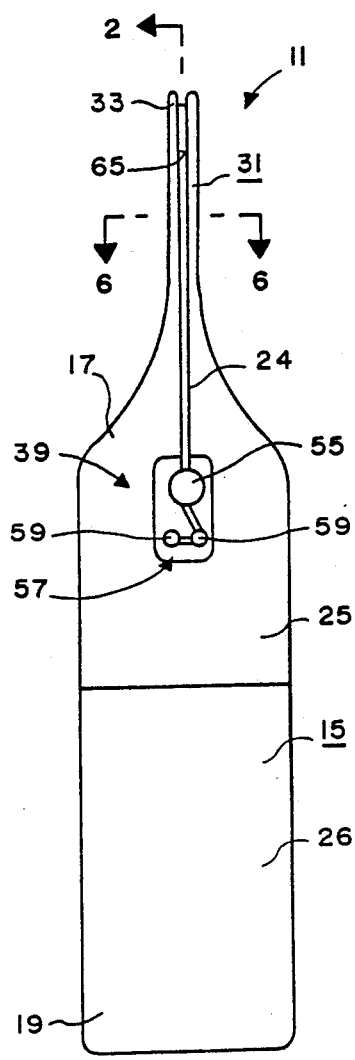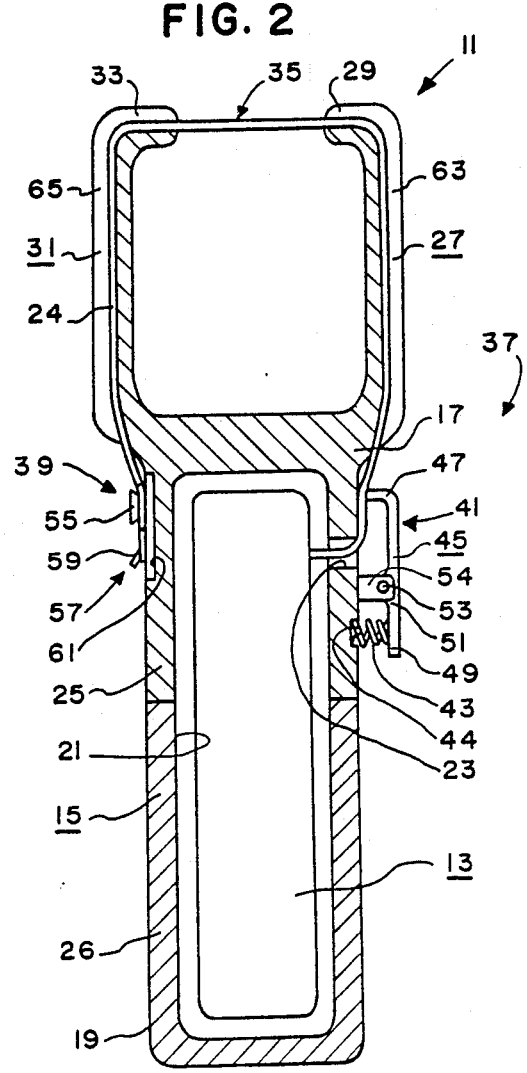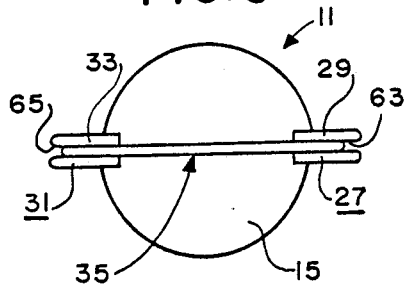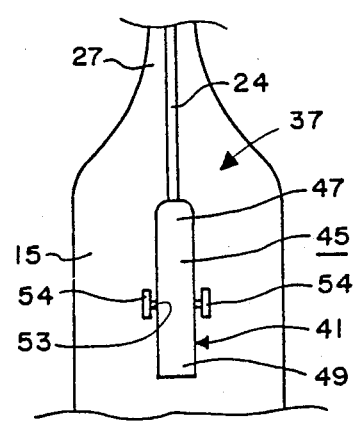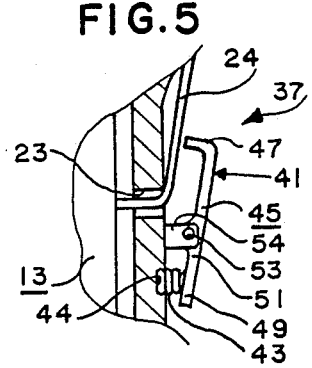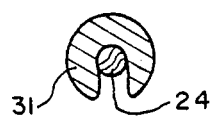

FLOSSING DEVICE

BACKGROUND OF THE INVENTION

1. Field of the Invention

The present invention relates, in general, to an improved flossing device.

2. Information Disclosure Statement

A preliminary patentability search in class 132, subclasses 324 and 325 produced the following patents: Perkins, U.S. Pat. No. 911,068; Kenyon, U.S. Pat. No. 1,174,016; Hochstadter, U.S. Pat. No. 1,465,669; Rose, U.S. Pat. No. 1,966,463; Spiegel et al, U.S. Pat. No. 1,733,631; Cohen, U.S. Pat. No. 2,644,469; and Bowden, U.S. Pat. No. 4,655,234. While the above patents disclose various dental floss dispensers and holders, none disclose or suggest the present invention. More specifically, none of the above patents disclose or suggest a flossing device including, in combination, handle means for being held by the user, the handle means having a forward end, having a hollow interior for holding the dental floss and having an aperture extending from the hollow interior for allowing the distal end of the dental floss to extend outward from the hollow interior; a first arm member extending outward from the forward end of the handle means, the first arm member having an outer end positioned a spaced distance from the forward end of the handle means; a second arm member extending outward from the forward end of the handle means, the second arm member having an outer end positioned a spaced distance from the forward end of the handle means and from the outer end of the first arm member; and positioning means for positioning a portion of the distal end of the dental floss between the outer end of the first arm member and the outer end of the second arm member and for holding the portion of the distal end of the dental floss tight between the outer end of the first arm member and the outer end of the second arm member, the positioning means including first lock means for locking the dental floss relative to the first arm member, and second lock means for locking the dental floss relative to the second arm member; one of the lock means being spring activated to automatically lock the dental floss relative to one of the arm members.

SUMMARY OF THE INVENTION

The present invention is directed toward providing an improved flossing device for use by a person in combination with dental floss to floss teeth. The floss device of the present invention includes, in general, handle means for being held by the user, the handle means having a forward end, having a hollow interior for holding the dental floss and having an aperture extending from the hollow interior for allowing the distal end of the dental floss to extend outward from the hollow interior; a first arm member extending outward from the forward end of the handle means, the first arm member having an outer end positioned a spaced distance from the forward end of the handle means; a second arm member extending outward from the forward end of the handle means, the second arm member having an outer end positioned a spaced distance from the forward end of the handle means and from the outer end of the first arm member; and positioning means for positioning a portion of the distal end of the dental floss between the outer end of the first arm member and the outer end of the second arm member and for holding the portion of the distal end of the dental floss tight between the outer end of the first arm member and the outer end of the second arm member, the positioning means including first lock means for locking the dental floss relative to the first arm member, and second lock means for locking the dental floss relative to the second arm member; the first lock means including a grip member movable between a first position in which the dental floss is locked relative to the first arm member and a second position in which the dental floss is free relative to the first arm member, and spring means for urging the grip member to the first position.

BRIEF DESCRIPTION OF THE DRAWINGS

FIG. 1 is a left side elevation of the flossing device of the present invention.

FIG. 2 is a sectional view substantially as taken on line 2—2 of FIG. 1.

FIG. 3 is a top plan view of the flossing device of the present invention.

FIG. 4 is a right side elevation of a portion of the flossing device of the present invention.

FIG. 5 is a view of a portion of FIG. 2 with parts of the flossing device shown in a moved position.

FIG. 6 is an enlarged sectional view substantially as taken on line 6—6 of FIG. 1 with portions thereof omitted for clarity.

DESCRIPTION OF THE PREFERRED EMBODIMENT

The flossing device 11 of the present invention is for use by a user in combination with dental floss 13 to floss teeth.

The flossing device 13 includes handle means 15 for being held by the user to facilitate use of the device 13. The handle means 15 preferably has an elongated, cylindrical shape for being easily held by the user. The handle means 15 preferably has a forward or first end 17 and a rearward or second end 19. The interior 21 of the handle means 15 is hollow for holding a supply of the dental floss 13. Typically, the dental floss 13 is provided by the manufacturer thereof in a tube or roll and the hollow interior 21 of the handle means 15 is sized and shaped so as to hold a typical tube or roll of dental floss as will now be apparent to those skilled in the art. A passageway or aperture 23 is provided through the wall of the handle means 13 into the hollow interior 21 thereof to allow the distal end 24 of the dental floss 13 to be threaded therethrough and extend outward from the hollow interior 13. The handle means 15 may be manufactured in various manners and of various materials as will now be apparent to those skilled in the art. Thus, the handle means 15 may be machined out of a metal such as aluminum, molded out of plastic, etc. Preferably, the handle means 15 is molded out of plastic as a two-piece unit with a first part 25 being at least partially separable from a second part 26 thereof to provide access to the hollow interior 21 and allow easy insertion of the dental floss 13 as will now be apparent to those skilled in the art.

The flossing device 11 includes a first arm member 27 extending downward from the forward end 17 of the handle means 15. The first arm member 27 has an outer end 29 positioned a spaced distance from the forward end 17 of the handle means 15. The first arm member 27 may be manufactured in various manners and of various materials as will now be apparent to those skilled in the art. Thus, the first arm member 27 may be machined out of a metal such as aluminum, molded out of plastic, etc. Preferably, the first arm member 27 is molded out of plastic as an integral, one-piece unit with the first part 25 of the handle means 15 as will now be apparent to those skilled in the art.

The flossing device 11 includes a second arm member 31 extending forward from the forward end 17 of the handle means 15. The second arm member 31 has an outer end 33 positioned a spaced distance from the forward end 17 of the handle means 15 and from the outer end 29 of the first arm member 27. The second arm member 31 may be manufactured in various manners and of various materials as will now be apparent to those skilled in the art. Thus, the second arm member 31 may be machined out of a metal such as aluminum, molded out of plastic, etc. Preferably, the second arm member 31 is molded out of plastic as an integral, one-piece unit with the first part 25 of the handle means 15 as will now be apparent to those skilled in the art.

The flossing device 11 includes positioning means for positioning a portion 35 of the distal end 24 of the dental floss 13 between the outer end 29 of the first arm member 27 and the outer end 33 of the second arm member 31 and for holding the portion 35 of the distal end 24 of the dental floss 13 tight between the outer end 29 of the first arm member 27 and the outer end 33 of the second arm member 31. The positioning means includes first lock means 37 for locking the dental floss 13 relative to the outer end 29 of the first arm member 27, and second lock means 39 for locking the dental floss 13 relative to the outer end 33 of the second arm member 31. One of the lock means 37, 39 is spring activated to automatically lock the dental floss 13 relative to one of the arm members 27, 31.

The first lock means 37 preferably includes a grip member 41 movable between a first position (see FIG. 2) in which the dental floss 13 is locked relative to the first arm member 27 and a second position (see FIG. 5) in which the dental floss 13 is free relative to the first arm member 27. The first lock means 37 preferably includes spring means 43 for urging the grip member 41 to the first position. The grip member 41 of the first lock means 37 preferably includes a lever member 45 having a first end 47, a second end 49, and a midportion 51. The grip member 41 preferably includes pivot means 53 for pivotally attaching the midportion 51 of the lever member 45 to the handle means 15. The pivot means 53 preferably consists of a pivot rod or the like extending outward of either side of the midportion 51 of the lever member 45 and pivotally coupled to a pair of spaced ear members 54 attached to the handle means 15 as clearly shown in FIGS. 2, 4 and 5 to allow the first end 47 of the lever member 45 to move toward and away from the outer surface of the handle means 15 as will now be apparent to those skilled in the art. The spring means 43 is preferably associated with the lever member 45 for normally urging the first end 47 of the lever member 45 toward the handle means 15 to tightly and fixedly clamp the dental floss 13 between the first end 47 of the lever member 45 and the handle means 15 as clearly shown in FIG. 2. Thus, the spring means 43 may be located between the second end 49 of the lever member 45 and the handle means 15 as clearly shown in FIGS. 2 and 5. The first end 47 of the lever member 45 moves away from the handle means 15 and releases the dental floss 13 when the user applies pressure to the second end 49 of the lever member 45 against the spring means 43 as will now be apparent to those skilled in the art. The lever member 45, pivot means 53 and ear members 54 may be manufactured in various manners and of various materials as will now be apparent to those skilled in the art. Thus, the lever member 45 and pivot means 53 may be machined out of metal, molded out of plastic, etc., and the ear members 54 are preferably constructed as an integral, one-piece unit with the first part 25 of the handle means 15 as will now be apparent to those skilled in the art. The spring means 43 preferably consists of a standard, off-the-shelf type coil spring or the like.

The second lock means 39 may consist simply of a button member 55 attached to the handle means 15 and about which the distal end 24 of the dental floss may be wrapped or tied to secure it relative to the outer end 33 of the second arm member 31 as will now be apparent to those skilled in the art. The structure and function of the button member 55 may be basically similar to that of the anchoring post 50 of Bowden, U.S. Pat. No. 4,655,234, issued Apr. 7, 1987. The button member 55 is preferably fixedly attached to the handle means 15 adjacent to the second arm member 33 as clearly shown in FIGS. 1 and 2.

The flossing device 11 preferably includes cutting means 57 for allowing the distal end 24 of the dental floss 13 to be cut from the remainder thereof. The cutting means 57 may consist of one or more knife-like projections 59 projecting from the handle means 15 for severing used portions of the dental floss 13 that is wedged thereinto in a manner as will now be apparent to those skilled in the art. The structure and function of the projections 59 may be basically similar to that of the cutter 44 of Bowden, U.S. Pat. No. 4,655,234, issued Apr. 7, 1987.

Both the second lock means 39 and the cutting means 57 may be manufactured in various manners and of various materials as will now be apparent to those skilled in the art. Preferably, both the second lock means 39 and the cutting means 57 are stamped or otherwise formed as an integral, one-piece unit out of metal and fixedly attached by glue or the like to the handle means 15 adjacent to the second arm member 31. An indentation 61 may be formed into the outer surface of the handle means 15 for receiving the unit as clearly shown in FIG. 2.

The positioning means preferably includes guide means for guiding the portion 35 of the dental floss 13 from the aperture 23 of the handle means 15 past the first lock means 37 to the outer end 29 of the first arm member 27, from the outer end 29 of the first arm member 27 to the outer end 33 of the second arm member 31, and from the outer end 33 of the second arm member 31 to the second lock means 39. The positioning means preferably includes a first groove 63 extending along the first arm member 27 for guiding the portion 35 of the dental floss 13 to the outer end 29 of the first arm member 27. The position means preferably includes a second groove 65 extending along the second arm member 31 for guiding the portion 35 of the dental floss 13 from the outer end 33 of the second arm member 31 to the button member 55 of the second lock means 39 and to the knife-like projections 59 of the cutting means 57. The grooves 63, 65 are preferably made into the arm members 27, 31 when the arm members 27, 31 are manufactured in any manner now apparent to those skilled in the art.

To use the flossing device 11 of the present invention, the distal end 24 of the dental floss 13 is first threaded through the aperture 23 and under the first end 47 of the lever member 45. With the second end 49 of the lever member 45 held down, the distal end 24 of the dental floss 13 is pulled from the interior 21 of the handle means 15, run under the first end 47 of the lever member 45, positioned or laid in the first and second grooves 63, 65, and positioned adjacent to the button member 55. The lever member 45 is then released to cause the first end 47 thereof to clamp a portion of the dental floss 13 tightly against the handle means 15 as clearly shown in FIG. 2. The distal end 24 of the dental floss 13 is then pulled tight and wrapped about or otherwise secured to the botton member 55, causing the portion 35 of the dental floss 13 to be held taut between the outer ends 29, 33 of the first and second arm members 27, 31. The prong-like arm members 27, 31 are then used to easily position the portion 35 of dental floss properly adjacent to the teeth to be flossed as will now be apparent to those skilled in the art. To replace the portion 35 of dental floss 13 with a fresh portion, the user merely pushes the second end 49 of the lever member 45 downward to release the dental floss 13 from the first lock means 37, unwraps or otherwise disengages the distal end 24 of the dental floss 13 from the button member 55 of the second lock means 39, pulls a fresh portion of dental floss 13 from the interior 21 of the handle means 15, releases the lever member 45, wraps or otherwise secures the dental floss 13 back to the button member 55 with the fresh portion 35 of dental floss 13 held taut between the outer ends 29, 33 of the first and second arm members 27, 31, and wedges the used portion of dental floss 13 against the knife-like projections 59 to cut it from the device 11 as will now be apparent to those skilled in the art.

Although the present invention has been described and illustrated with respect to a preferred embodiment and a preferred use therefor, it is not to be so limited since modifications and changes can be made therein which are within the full intended scope of the invention.

I claim:

1. A flossing device for use by a user in combination with dental floss to floss teeth, said flossing device comprising:
   (a) handle means for being held by the user, said handle means having a forward end, having a hollow interior for holding said dental floss and having an aperture extending from said hollow interior for allowing the distal end of said dental floss to extend outward from said hollow interior;
   (b) a first arm member extending outward from said forward end of said handle means, said first arm member having an outer end positioned a spaced distance from said forward end of said handle means;
   (c) a second arm member extending outward from said forward end of said handle means, said second arm member having an outer end positioned a spaced distance from said forward end of said handle means and from said outer end of said first arm member; and
   (d) positioning means for positioning a portion of said distal end of said dental floss between said outer end of said first arm member and said outer end of said second arm member and for holding said portion of said distal end of said dental floss tight between said outer end of said first arm member and said outer end of said second arm member, said positioning means including first lock means for locking said dental floss relative to said first arm member, and second lock means for locking said dental floss relative to said second arm member; said first lock means including a grip member movable between a first position in which said dental floss is locked relative to said first arm member and a second position in which said dental floss is free relative to said first arm member, and spring means for urging said grip member to said first position; said grip member including a lever member having a first end, a second end, and a midportion; said grip member including pivot means for pivotally attaching said midportion of said lever member to said handle means; said spring means being associated with said lever member for normally urging said first end of said lever member toward said handle means to clamp said dental floss between said first end of said lever member and said handle means; said first end of said lever member moving away from said handle means and releasing said dental floss when the user applies pressure to said second end of said lever member against said spring means.

2. The flossing device of claim 1 in which said positioning means includes guide means for guiding said portion of said dental floss from said aperture of said handle means past said first lock means to said outer end of said first arm member, from said outer end of said first arm member to said outer end of said second arm member, and from said outer end of said second arm member to said second lock means.

3. The flossing device of claim 2 in which said positioning means includes a first groove for guiding said portion of said dental floss to said outer end of said first arm member, and includes a second groove for guiding said portion of said dental floss from said outer end of said second arm member.

4. The flossing device of claim 3 in which is included cutting means for allowing a distal end portion of said dental floss to be cut from the remainder thereof.

* * * * *